(12) United States Patent
Becerro De Bengoa Vallejo

(10) Patent No.: US 6,171,811 B1
(45) Date of Patent: Jan. 9, 2001

(54) **METHOD AND KIT FOR DETECTING *HELICOBACTER PYLORI***

(75) Inventor: Ana Becerro De Bengoa Vallejo, Madrid (ES)

(73) Assignee: Isomed, S.L., Madrid (ES)

( * ) Notice: Under 35 U.S.C. 154(b), the term of this patent shall be extended for 0 days.

(21) Appl. No.: 09/101,992

(22) PCT Filed: Jul. 21, 1997

(86) PCT No.: PCT/ES97/00184
§ 371 Date: Jul. 20, 1999
§ 102(e) Date: Jul. 20, 1999

(87) PCT Pub. No.: WO98/21579
PCT Pub. Date: May 22, 1998

(30) Foreign Application Priority Data

Nov. 12, 1996 (ES) .................................................... 9602383

(51) Int. Cl.[7] ................. C12Q 1/04; C12Q 1/02; G01N 33/53
(52) U.S. Cl. ................. 435/34; 435/29; 435/975; 435/968
(58) Field of Search ................. 435/34, 29, 975, 435/968

(56) References Cited

PUBLICATIONS

Graham et al, "Am. J. Gastroenterol.", vol. 94(5), pp. 1214–1217 (Abstract Only), 1999.*

Lotterer et al, "Z. Gastroenterol.", vol. 29(11), pp. 590–594, (Abstract Only), 1991.*

* cited by examiner

Primary Examiner—Louise N. Leary
(74) Attorney, Agent, or Firm—Darby & Darby

(57) ABSTRACT

The method is based on the carbon-13 labelled urea breath test, which comprises a) administering to the patient an aqueous solution of citric acid at pH comprised between 2 and 2.5; b) collecting a sample of the patient's breath with the object of determining the baseline content of carbon-13; c) administering to the patient a suitable amount of carbon-13 labelled urea; d) collecting a sample of the patient's breath with the object of determining the content of carbon-13 after the administration of the labelled urea; and e) analyzing the breath samples collected to determine the carbon-13 content before and after the administration of urea labelled with carbon-13. The kit has a container for the citric acid, another for the carbon-13 labelled urea, exetainers destined to containing the patient's breath, and means to blow the breath into the exetainers.

37 Claims, 1 Drawing Sheet

METHOD AND KIT FOR DETECTING HELICOBACTER PYLORI

FIELD OF THE INVENTION

The invention refers to a method for the detection of *Helicobacter pylori,* based on the $^{13}$C-labelled urea breath test, and a kit for carrying out said method. This method can be used in the diagnosis of gastroduodenal diseases associated with *Helicobacter pylori.*

BACKGROUND OF THE INVENTION

*Helicobacter pylori* is a Gram negative bacillus which was isolated for the first time in 1982, and the presence of which in the organism has been associated with gastroduodenal diseases. More specifically, this bacillus is the main responsible for the development of duodenal peptic ulcer, as well as the main causative agent of chronic gastritis, where it appears in 90–95% of the patients, its presence also being detected in patients with duodenal ulcer, gastric ulcer, dyspepsia, gastric non-Hodgkin's lymphomas and even cases of gastric cancer.

With the object of establishing a proper and effective treatment of a possible gastroduodenal disease, it is necessary to carry out an accurate and reliable diagnosis of the same. Some methods for the diagnosis of gastroduodenal diseases are based upon the detection of *Helicobacter pylori* by methods that can be divided into invasive and non-invasive methods. Invasive methods require the performance of an endoscopy on the patient and the subsequent realisation of histological studies, cultures or the rapid urease test on samples of the gastric mucosa collected by endoscopic biopsy. Although these methods have an adequate sensitivity and specificity, they are expensive, they require trained personnel for carrying them out and produce discomfort to the patient who, occasionally, rejects them. Among the non-invasive methods it is possible to count the serological methods and the urea breath test. In general, the serological methods exhibit less sensitivity and specificity than the urea breath test and, additionally, only detect antibodies against *H. pylori* and not the presence of the same, as the $^{13}$C-labelled urea breath test does. The serological test is not reliable for monitoring the effectiveness of an eradicating treatment because a significant decrease in the antibody titre is appreciable after the sixth month post-eradication, without there being any certainty before the eighteenth month post-eradication, whereas, with the breath test it is possible to demonstrate with certainty the elimination of *H. pylori* by the treatment, starting from the first month after having concluded the same.

The urea breath test is based upon the fact that an abnormal urease activity is observed in numerous gastroduodenal diseases, particularly in those related with the presence of *H. pylori,* and hence, the detection of urease activity in abnormal amounts is indicative of the existence of *H. pylori*, and consequently, of a possible gastroduodenal pathology. Urease (urea amidohydrolase) is an enzyme which catalyses the hydrolysis of urea (carbonyldiamide) into ammonium carbonate which decomposes into carbon dioxide and ammonia. In order to carry out the urea breath test, the patient is administered urea, which is optionally labelled with carbon-13 ($^{13}$C), carbon-14 ($^{14}$C), or with nitrogen-15 ($^{15}$N), and the breath of the patient is subsequently analysed to detect the presence of products resulting from the hydrolysis of the labelled urea. The carbon dioxide labelled with carbon-13 or carbon-14, produced by the hydrolysis of the urea labelled with said isotopes, is absorbed by the blood system, transported to the lungs and is finally exhaled, making its detection possible in the breath of the patient.

The U.S. Pat. No. 4,830,010, held by B. J. Marshall, discloses a method for the diagnosis of gastroduodenal diseases based on the urea breath test, which presents numerous drawbacks, some of which are:

- the use of solutions prior to the administration of urea which do not reproduce the pH in the stomachal antrum (between 2 and 2.3) which is suitable to maintain *H. pylori* in its environment, and, therefore, the results obtained are of dubious accuracy and reliability, and, additionally, these solutions often produce gastroduodenal disorders in the patient, such as diarrhoea, sensation of heaviness in the stomach, vomits, etc.;

- the use of urea labelled with carbon-14, a radioactive isotope, which increases the cost of the method and considerably limits its field of application, as it cannot be used on pregnant women or on children, not being it possible to repeat the test in the same patient more than two or three times due its radioactivity;

- the dosing of the labelled urea, as a function of the weight of the patient, entails a certain degree of complexity in carrying out the assay, as well as a greater consumption of the reagent with the consequent repercussions, not only at the economical level, but also in relation to the existence of a certain degree of risk due to toxicity and or adverse effects on the patient;

- the patient must remain in the horizontal position throughout all of the duration of the test, which can result in discomfort to the patient; and

- the collection of the patient's breath is carried out in plastic bags by the use of plastic mouth-pieces and subsequently the air is removed from the bags by the use of syringes and a Vacutainer® (a pressurised glass tube fitted with a rubber stopper, which on the long term may interfere with the gases produced from the air of the patient collected in the tube) is introduced. The large number of components necessary to collect the breath of the patient not only complicates the performance of the assay but also increases its cost, as in addition to the cost of the components, the cost of treating to the wastes generated, so as to avoid environmental problems, must be considered.

Consequently, the method described in the U.S. Pat. No. 4,830,010 is a general method, not very specific, and of dubious reliability and reproducibility, which has a limited field of application, is complex, expensive and a nuisance and a source of discomfort for the patient.

The present invention provides a method and a kit for carrying out a breath test with urea labelled with carbon-13, for the detection of *H. pylori,* which overcomes the disadvantages which where mentioned above. Particularly, the invention provides an assay for the detection of *H. pylori* which is simple, easy to conduct, reliable, reproducible, of wide application, uncomplicated, cost-effective, safe and comfortable for the patient.

DETAILED DESCRIPTION OF THE INVENTION

Figure 1:
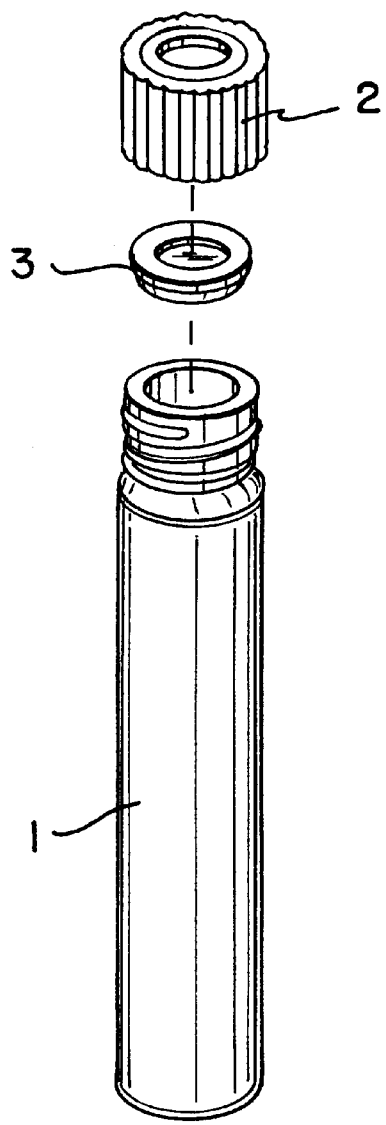
FIG. 1 shows a drawing of an exetainer of the kind used in the kit object of the present invention, which shows, separately, the different components of the exetainer.

1. Method for the detection of *Helicobacter pylori*

In a first object of this invention, a method is provided for the detection of *Helicobacter pylori*, based on the carbon-13 labelled urea breath test, which comprises the general stages of:

administering a suitable amount of urea labelled with carbon-13 to the patient; and determining the carbon-13 content in samples of the patient's breath, before and after the administration of urea labelled with carbon-13;

characterised in that:

an aqueous solution of citric acid which comprises citric acid in an amount sufficient to yield a pH comprised between 2 and 2.5 is administered to the patient;

the carbon-13 content in the sample of the patient's breath, prior to the administration of urea labelled with carbon-13, can be carried out before, or alternatively, after, administering said aqueous solution of citric acid to the patient; and;

the urea labelled with carbon-13 can be administered to the patient after, or simultaneously with, the administration of said aqueous solution of citric acid.

A first embodiment of the method for the detection of *Helicobacter pylori* based on the carbon-13 labelled urea breath test, provided by the present invention, involves the administration to the patient of the aqueous solution of citric acid prior to determining the baseline level of carbon-13 in the sample of breath and before the administration of the urea labelled with carbon-13, which comprises the stages of:

a) administering to the patient an aqueous solution of citric acid which comprises citric acid in an amount sufficient to yield a pH comprised between 2 and 2.5;

b) collecting a sample of the patient's breath with the object of determining the baseline content of carbon-13;

c) administering to the patient a suitable amount of urea labelled with carbon-13;

d) collecting a sample of the patient's breath with the object of determining the content of carbon-13 after the administration of the urea labelled with carbon-13; and e) analysing the breath samples collected to determine the carbon-13 content before and after the administration of urea labelled with carbon-13.

The aqueous solution of citric acid comprises a solution of citric acid in water in an amount sufficient to yield a pH comprised between 2 and 2.5. Normally, such a pH is attained with an aqueous solution of citric acid at a concentration of approximately 0.021 g/ml. The use of this solution fulfils two objectives, on the one hand it contributes to delaying gastric emptying, which permits the carbon-13 labelled urea to remain for longer in the stomachal antrum, and, in the other hand, by yielding a pH which mimics that of the stomachal antrum, it makes it possible for the colony of *H. pylori* to more effectively exert its urease activity, hydrolysing the urea into carbon dioxide and water. The use of this solution is essential and critical for the assay to be significantly effective, sensitive, reliable and reproducible, and it constitutes one of the essential aspects of the invention.

The aqueous solution of citric acid may additionally contain acceptable pharmaceutical and food additives which improve its organoleptic properties and characteristics, such as for example, sweeteners, flavours, colorants and preservatives.

Said aqueous solution of citric acid can be easily obtained by dissolution of the components in a suitable amount of water. In a specific and preferred embodiment of the method object of the invention, the aqueous solution of citric acid is obtained by dissolving an amount comprised between 2 and 5 g of citric acid in a suitable amount of water.

In another specific embodiment of the method object of the present invention, the possibility of using fruit juices, for example of citrus fruits (orange, lemon, grapefruit, etc.) as a source of said aqueous solution of citric acid is considered, as long as said juice has a pH comprised between 2 and 2.5. In the event that the juice should not have such a pH, it would be possible to add acceptable pharmaceutical or food acidifiers in the necessary amount to attain said pH.

The use of an aqueous solution of citric acid which comprises citric acid in an amount sufficient to yield a pH comprised between 2 and 2.5, optionally together with other acceptable pharmaceutical or food additives, in the performance of a method for the detection of *H. pylori*, based on the testing of breath with urea labelled with carbon-13, constitutes an additional object of the present invention.

After the administration of the aqueous solution of citric acid, samples of the patient's breath are collected in suitable containers, such as exetainers, with the object of determining the baseline content of carbon-13. As it is well know, carbon-13 is an isotope which is normally present at very small amounts in natural products, such as urea originating from protein metabolism. Generally, the carbon atoms present in a sample of naturally occurring urea are mostly constituted by the carbon-12 isotope and a very small amount of the carbon-13 isotope (approximately 1.1%). Duplicate samples are normally collected some 10 minutes after the administration of the aqueous solution of citric acid. The suitable containers are preferably exetainers of the kind shown in FIGS. 1 and 2, the characteristics of which are discussed in greater detail when dealing with the kit provided by the present invention. In a specific and preferred embodiment of the method object of this invention, the patient introduces his breath into the exetainers by blowing with the aid of a straw, which is previously introduced in them, being the exetainer subsequently closed by means of its stopper.

Subsequently the patient is administered a suitable amount of carbon-13 labelled urea. The term "suitable amount" refers to a safe and effective amount of carbon-13 labelled urea which is sufficient to produce a detectable level of carbon dioxide labelled with carbon-13, without producing adverse effects such as toxicity or allergic reactions in the patient.

The carbon-13 labelled urea is normally administered in the form of an aqueous solution after its dissolution in water. In a specific embodiment of the method of the present invention, an amount of carbon-13 labelled urea comprised between 50 and 100 mg is dissolved in an amount of water comprised between 20 and 50 ml. In a preferred embodiment, the patient is administered an aqueous solution of carbon-13 labelled urea at a concentration comprised between 1 and 4.5 mg/ml. Alternatively, the carbon-13 labelled urea can be administered in the form of a tablet, optionally dispersible, which contains a suitable amount of carbon-13 labelled urea.

This dosage, regardless of the weight, constitutes an operational simplification as well as an important economical saving, as it reduces the consumption of reagent, considering that, for example, in order to carry out the assay provided by the present invention on an adult of 70 kg of weight, 100 mg of carbon-13 labelled urea can be used up, whereas in other assays corresponding to the state of the art, in which the dosage is a function of the body weight (typically 2 mg/kg of body weight), an adult of 70 kg of weight requires 140 mg of carbon-13 labelled urea. The use of smaller amounts of carbon-13 labelled urea produces a smaller risk of toxicity and adverse effects on the patient. All of this makes the assay of the invention a simpler, more cost-effective, and safer than other similar assays known. On the other hand, the use of carbon-13 labelled urea presents the advantage of that, not being radioactive, it can be administered both to adults and children, and even to pregnant women, and additionally, it can be repeated as many times as necessary in the same patient. Furthermore, its realisation does not require any special installations, and the samples can be delivered to other centres for their reading, by ordinary mail or via any other means, without the need of special care.

The carbon-13 labelled urea is a commercial product, available in the form of a powder, tablets and other presentations, manufactured by, for example, Cambridge Isotope Laboratories, Inc.

After the administration of the aqueous solution of carbon-13 labelled urea, samples of the patient's breath are collected in suitable containers, such as the exetainers mentioned above, with the object of determining the carbon-13 content after the administration of the urea labelled with said isotope. Generally, duplicate samples are collected after allowing the urease activity to act for a suitable period of time, normally about 30 minutes. The patient introduces his breath into the exetainers by blowing with the aid of a straw as has been mentioned previously.

The exetainers with the breath samples collected can be stored at room temperature for several months without adversely affecting the content of the patient's breath.

The breath samples collected in the containers are delivered to a laboratory to carry out an analysis on the breath and so determine the carbon-13 content before and after the administration of carbon-13 labelled urea, by means of the use of the appropriate techniques. In a specific invention, the separation of the gases is carried out by gas chromatography and the determination of carbon-13 is carried out by mass spectrometry.

A second embodiment of the method for the detection of *Helicobacter pylori*, based on the carbon-13 labelled urea breath test, provided by the present invention, involves the determination of the baseline level of carbon-13 in the sample of breath before the administration of the aqueous solution of citric acid and of urea labelled with carbon-13, and simultaneously administering to the patient the aqueous solution of citric acid and carbon-13 labelled urea, which comprises the steps of:

a) collecting a sample of the patient's breath with the object of determining the baseline content of carbon-13;

b) simultaneously administering to the patient:
   an aqueous solution of citric acid which comprises citric acid in an amount sufficient to yield a pH comprised between 2 and 2.5;
   and a suitable amount of urea labelled with carbon-13;

c) collecting a sample of the patient's breath with the object of determining the content of carbon-13 after the administration of the solution of citric acid and of urea labelled with carbon-13; and d) analysing the breath samples collected to determine the carbon-13 content before and after the administration of urea labelled with carbon-13.

By performing this second alternative, the duration of the assays is reduced by approximately 10 minutes and a step is eliminated, due to the simultaneous administration of the aqueous solution of citric acid and the urea labelled with carbon-13.

The collection of breath samples from the patient prior to administering to him the aqueous solution of citric acid and the urea labelled with carbon-13, with the object of determining the baseline carbon-13 content, is carried out in exetainers as was mentioned previously in the first alternative embodiment of the method for the detection of *H. pylori* object of the present invention.

Subsequently, the patient is administered simultaneously the aqueous solution of citric acid and the suitable amount of carbon-13 labelled urea. As in the case of the first alternative, the aqueous solution of citric acid comprises a solution in water of citric acid in a sufficient amount to yield a pH comprised between 2 and 2.5 and it may contain, additionally, acceptable pharmaceutical and food additives which improve its organoleptic properties and characteristics, such as, sweeteners, flavours, colorants and preservatives. The carbon-13 labelled urea is administered either in the form of an aqueous solution after its dissolution in water, or in the form of a tablet. In a specific embodiment of the method object of the invention, an amount of carbon-13 labelled urea comprised between 50 and 100 mg, optionally dissolved in an amount of water comprised between 20 and 50 ml, is administered.

After the administration of the citric acid and the carbon-13 labelled urea, the patient's breath samples are collected in exetainers with the object of determining the carbon-13 content after the administration of urea labelled with said isotope. Generally, duplicate samples are collected after allowing the urease activity to act for a suitable period of time, normally about 30 minutes. The patient introduces his breath into the exetainers by blowing with the aid of a straw as has been mentioned previously.

The exetainers with the breath samples collected can be stored at room temperature for several months without adversely affecting the content of the patient's breath.

The breath samples collected in the containers are delivered to a laboratory to carry out an analysis on the breath and so determine the carbon-13 content before and after the administration of carbon-13 labelled urea, by means of the use of the appropriate techniques, such as gas chromatography and mass spectrometry.

In general, in order to carry out the method for the detection of *H. pylori* object of the present invention, in any of its alternative embodiments, it is convenient that the patient has fasted, being it advisable that the patient has not eaten any kind of food in the 6–8 h prior to the performance of the test.

The comparison between the baseline carbon-13 content and the carbon-13 content after the administration of carbon-13 labelled urea allows to evaluate the urease activity. A high, low or non-existent urease activity (cut-off or reference point: 3–5) can be indicative of a micro-organism with urease activity, such as *H. pylori* and, therefore, it can be indicative of the existence of a gastroduodenal disease.

Consequently, a specific application of the method for the detection of *H. pylori* provided by the present invention consists in the diagnosis of the infection by *H. pylori*, the direct causative agent of the gastroduodenal diseases mentioned previously, by means of a non-invasive method based upon the carbon-13 labelled urea breath test. Therefore, the method for the detection of *H. pylori* provided by this invention can be used in the diagnosis of gastroduodenal diseases such as duodenal peptic ulcer, duodenal ulcer, gastric ulcer, dyspepsia, non-Hodgkin's gastric lymphomas and even stomach cancer.

Another application of the method for the detection of *H. pylori* object of this invention is that of checking the evolution of the treatment of the gastroduodenal disease and, particularly, the eradication of *H. pylori*, as it allows the determination of the eradication of *H. pylori* even within a maximum one month after the treatment, without giving rise to false negatives as it happens with the serological methods.

The method for the detection of *H. pylori* provided by this invention, in any of its alternative embodiments, presents numerous advantages over other similar known methods, considering that:

- it is a non-invasive method, and therefore its does not require the performing of a gastroscopy on the patient;
- it is safe, as it uses a stable and non-radioactive isotope (carbon-13) in moderate amounts;
- it is reliable and reproducible, as it reproduces the standard conditions of the environment of the stomachal antrum, ensuring the survival of the possible colony if *H. pylori*;
- it is effective, as it reflects the infection of all the surface of the stomach;
- it is fast, as it provides results in 48 hours;
- it is easy, simple, it does not require qualified personnel and, in fact, it can be carried out in practice or hospital of the doctor as well as in the patient's own home, sending the closed containers with the different breath samples to the analytical laboratory;
- it is comfortable, as the patient is not obliged to maintain a specific position throughout the development of the assay, and in fact, the patient does not have to remain in a horizontal position during the test, as in other assays of the sate of the art, and he can change posture and be seated or standing, with the only limitation that he may not smoke nor eat or drink throughout the test;
- the collection of the breath is very simple and cost-effective; and
- it has widespread application, as it can be applied on pregnant women, children, adults and elderly.

2. Kit for the detection of *H. pylori*

In a second object, a kit is provided for the detection *Helicobacter pylori*, in particular, a kit for carrying out a method based on the carbon-13 labelled urea breath test described above. In its simplest form the kit comprises a case which contains:

- a container containing carbon-13 labelled urea;
- at least two containers destined to containing the breath of the patient, one of which is destined to containing the breath of the patient after the administration of the citric acid but before the administration of the carbon-13 labelled urea, while the other container is destined to containing the breath of the patient after the administration of the carbon-13 labelled urea, being said containers constituted by glass tubes provided with screw-cap stoppers fitted with a septum; and
- the means to blow the breath into the aforementioned containers.

The kit may, or may not, include additionally, a container containing citric acid, which can be in the solid state, in an amount such that after dissolution in a suitable amount of water, will yield a pH comprised between 2 and 2.5. In this specific case, the container containing the citric acid is a sachet or the like. Alternatively and optionally, the container may contain, in addition to the citric acid, acceptable pharmaceutical or food additives (sweeteners, flavours, preservatives and colorants). Therefore, in a specific embodiment of the kit object of the present invention, a sachet is provided which contains between 2 and 5 g of citric acid, typically 4.2 g of citric acid, optionally together with other additives, for its dissolution into 200 ml of water.

The container which contains the carbon-13 labelled urea can be a sachet containing the suitable amount of carbon-13 labelled urea in powdered form, or a blister containing a tablet of carbon-13 labelled urea at the appropriate dose, or, alternatively, a closed flask which contains the suitable amount of carbon-13 labelled urea, whereupon said flask has the suitable volume to obtain the aqueous solution of carbon-13 labelled urea at the desired concentration. In a specific embodiment, the container which contains the carbon-13 labelled urea is a flask of at least 20 to 50 ml, which contains between 50 and 100 mg of powdered carbon-13 labelled urea. In another specific embodiment, said container is a blister which contains a tablet, optionally dispersible, which contains between 75 and 100 mg of carbon-13 labelled urea.

Figure 2:
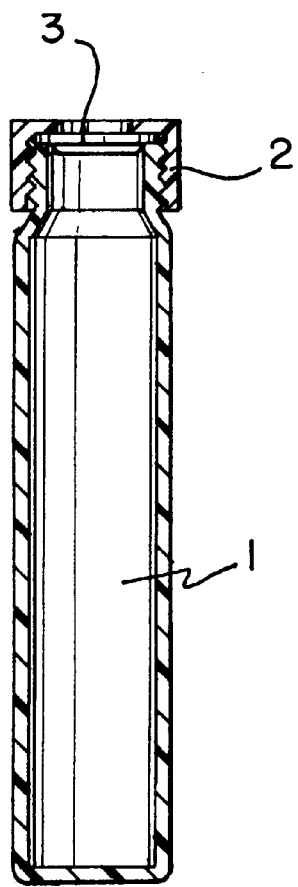
FIG. 2 shows a drawing of an exetainer of the type shown in FIG. 1, with all its components assembled.

The containers destined to containing the breath of the patient are exetainers as those shown in FIGS. 1 and 2, where it can be seen that said exetainers are constituted by a tube (1), preferably made of glass, the stoppers of which (2) are threaded and have a septum (3)in the centre, made of an elastomer suited for pharmaceutical purposes, which permits its penetration by means of a needle which collects the air contained in the exetainer for its subsequent analysis. The septum (3) is specially designed so that the needle of the air-collecting machine may pierce and carry out its task successive times without breaking.

In order to assess the reliability and the reproducibility of the assay object of this invention it is important to collect duplicate breath samples, both before and after the administration of carbon-13 labelled urea, and hence, the kit of the invention will, contain, preferably, four exetainers, of which two will be used to collect the patient's breath after the administration of the citric acid but before the administration of the carbon-13 labelled urea, while the other two will collect the patient's breath after the administration of the carbon-13 labelled urea. In order to facilitate the interpretation of the results obtained, it is important that the exetainers bear a mark which makes it possible to distinguish between the ones which collect the breath from before the administration the carbon-13 labelled urea and those that collect the breath from after the administration of the carbon-13 labelled urea.

Generally, the means for blowing the breath into the containers are straws or similar devices.

Therefore, in a specific and preferred embodiment of this invention a kit is provided for the detection of *H. pylori*, in particular, a kit for carrying out the previously disclosed carbon-13 labelled urea breath test, which comprises a case which contains:

- a sachet containing citric acid, in the solid state, in a quantity sufficient so that, after dissolution in a suitable amount of water, it yields a pH comprised between 2 and 2.5, together with optionally, some additives, such as sweeteners, flavours, preservatives and colorants;
- a flask containing the suitable amount of carbon-13 labelled urea, in powdered form, said flask containing the necessary volume to dissolve the urea and achieve the desired concentration, or alternatively, a blister containing a tablet with the suitable amount of carbon-13 labelled urea;
- four exetainers destined to contain the breath of the patient, two of which are used to collect the patient's breath after the administration of the citric acid but before the administration of the aqueous solution of carbon-13 labelled urea, while the other two will collect the patient's breath after the administration of the aqueous solution of carbon-13 labelled urea; and some straws to blow the breath into the exetainers.

Advantageously, the exetainers will be labelled so that it may be possible to distinguish easily between the exetainers destined for use in collecting the breath before the administration the carbon-13 labelled urea from those used to collect the breath after the administration of the carbon-13 labelled urea.

The following examples illustrate the invention.

EXAMPLE 1

Preparation of an Aqueous Solution of Citric Acid

An aqueous solution of citric acid at a pH comprised between 2 and 2.5 is prepared by dissolving, in 200 ml of water, a mixture formed by:

|  | Grams | Percentage |
| --- | --- | --- |
| Citric acid | 4.2 | 96.1 |
| Sodium carbonate | 0.1 | 2.24 |
| Lemon flavour (powder) | 0.04 | 0.9 |
| Aspartame | 0.03 | 0.67 |
| Sunset-Yellow | 0.002 | 0.04 |
| TOTAL | 4.472 | 99.95 |

EXAMPLE 2

Assay for the Detection of *H. pylori*

A patient suspect of suffering a gastroduodenal disease related with *H. pylori*, is subjected to the assay described hereunder. The assay is carried out on an adult patient, who has fasted for 8 hours.

The patient was administered 200 ml of an aqueous solution of citric acid, like the one prepared in Example 1. After 10 minutes, duplicate samples of the patient's breath are collected into exetainers labelled as "BASELINE" which are used to determine the baseline carbon-13 content. In order to collect the breath, the patient makes use of a straw previously placed within the exetainer and he gently blows the exhaled air until condensation caused by the breath appears on the internal walls of the exetainer, and subsequently keeps on exhaling his breath at the same time as he removes the straw and finally closes the exetainer by means of the corresponding stopper.

Subsequently, the patient is administered 50 ml of an aqueous solution of carbon-13 labelled urea [Cambridge Isotope Laboratories, Inc.], at a concentration of 1.5 mg/ml. After 30 minutes duplicate breath samples are collected from the patient, as mentioned above, in exetainers marked with the label "POST", which are used to determine the carbon-13 content after the administration of urea labelled with said isotope.

The exetainers are sent to an analytical laboratory to analyse the breath samples collected and so determine the carbon-13 content before and after the administration of carbon-13 labelled urea. In order to do this the samples are sent to an automatic breath carbon analyser (ABCA) [Europa Cientifica, S.L] prior extraction of the air contained in the exetainers with the aid of a needle which pierces the septum of the stopper without breaking. The gases contained in the breath samples are separated by gas chromatography and the carbon-13 content is determined by mass spectroscopy following the manufacturers instructions.

The comparison between the carbon-13 baseline content [BASELINE] and the carbon-13 content after administrating the carbon-13 labelled urea [POST] allows the doctor to assess the urease activity and consequently the diagnosis of a possible gastroduodenal disease associated with the presence of *H. pylori*.

I claim:

1. A method for the detection of *Helicobacter pylori*, based on the carbon-13 labelled urea breath test, which comprises the stages of:

a) administering to the patient an aqueous solution of citric acid which comprises citric acid in an amount sufficient to yield a pH comprised between 2 and 2.5;

b) collecting a sample of the patient's breath with the object of determining the baseline content of carbon-13;

c) administering to the patient a suitable amount of carbon-13 labelled urea;

d) collecting a sample of the patient's breath with the object of determining the content of carbon-13 after the administration of the carbon-13 labelled urea; and e) analysing the breath sample collected to determine the carbon-13 content before and after the administration of carbon-13 labelled urea.

2. The method according to claim 1, wherein said aqueous solution of citric acid comprises, additionally, acceptable pharmaceutical or food additives, selected from the group formed by sweeteners, flavors, colorants and preservatives.

3. The method according to claim 1, wherein said aqueous solution of citric acid originates from a fruit juice, optionally acidified with an acceptable pharmaceutical or food acidifier.

4. The method according to claim 1, wherein the collection of the patient's breath samples for determining the baseline carbon-13 content is carried out approximately 10 minutes after the administration of the aqueous solution of citric acid.

5. The method according to claim 1, wherein the carbon-13 labelled urea is administered in the form of an aqueous solution.

6. The method according to claim 5, wherein said aqueous solution of carbon-13 labelled urea has a concentration comprised between 1 and 4.5 mg/ml.

7. The method according to claim 1, wherein the carbon-13 labelled urea is administered in the form of a tablet.

8. The method according to claim 7, wherein said tablet contains between 50 and 100 mg of carbon-13 labelled urea.

9. The method according to claim 1, wherein the collection of the patient's breath samples for determining the carbon-13 content after the administration of the carbon-13 labelled urea is carried out approximately 30 minutes after the administration of the carbon-13 labelled urea.

10. The method according to claim 1, wherein the patient's breath is collected in exetainers.

11. The method according to claim 1, wherein the analysis of the breath and the determination of the carbon-13 content is carried out by gas chromatography and mass spectroscopy.

12. The method according to claim 1, wherein the comparison between the baseline carbon-13 content and the carbon-13 content after administration of carbon-13 labelled urea is indicative of the urease activity existing in the patient.

13. The method for the detection of *Helicobacter pylori*, based on the carbon-13 labelled urea breath test, which comprises the steps of:
   a) collecting a sample of the patient's breath with the object of determining the baseline content of carbon-13;
   b) simultaneously administering to the patient:
      an aqueous solution of citric acid which comprises citric acid in an amount sufficient to yield a pH comprised between 2 and 2.5; and
      a suitable amount of carbon-13 labelled urea;
   c) collecting a sample of the patient's breath with the object of determining the content of carbon-13 after the administration of the solution of citric acid and of carbon-13 labelled urea; and
   d) analysing the breath samples collected to determine the carbon-13 content before and after the administration of carbon-13 labelled urea.

14. The method according to claim 13, wherein said aqueous solution of citric acid comprises, additionally, acceptable pharmaceutical or food additives, selected from the group formed by sweeteners, flavours, colorants and preservatives.

15. The method according to claim 13, wherein said aqueous solution of citric acid originates from a fruit juice, optionally acidified with an acceptable pharmaceutical or food acidifier.

16. The method according to claim 13, wherein the carbon-13 labelled urea is administered dissolved in an aqueous solution.

17. The method according to claim 16, wherein said aqueous solution of carbon-13 labelled urea has a concentration comprised between 1 and 4.5 mg/ml.

18. The method according to claim 13, wherein the carbon-13 labelled urea is administered in the form of a tablet.

19. The method according to claim 18, wherein said tablet contains between 50 and 100 mg of carbon-13 labelled urea.

20. The method according to claim 13, wherein the collection of the patient's breath samples for determining the carbon-13 content after the administration of the carbon-13 labelled urea is carried out approximately 30 minutes after the administration of the carbon-13 labelled urea.

21. The method according to claim 13, wherein the patient's breath is collected in exetainers.

22. The method according to claim 13, wherein the analysis of the breath and the determination of the carbon-13 content is carried out by gas chromatography and mass spectroscopy.

23. The method according to claim 13, wherein the comparison between the baseline carbon-13 content and the carbon-13 content after administration of carbon-13 labelled urea is indicative of the urease activity existing in the patient.

24. A kit for the detection of *Helicobacter pylori*, by carrying out a method based on the carbon-13 labelled urea breath test according to claim 1, which comprises a case which contains:
   a container containing carbon-13 labelled urea;
   at least, two containers destined to containing the breath of the patient, one of which is destined to containing the breath of the patient after the administration of the citric acid but before the administration of the carbon-13 labelled urea, while the other container is destined to containing the breath of the patient after the administration of the carbon-13 labelled urea, being said containers constituted by glass tubes provided with screw-cap stoppers fitted with a septum; and
   the means to blow the breath into the aforementioned containers.

25. The kit according to claim 24, which additionally comprises a container which contains citric acid.

26. The kit according to claim 25, wherein the citric acid is in the solid state, in an amount such that after dissolution in a suitable amount of water, it yields a pH comprised between 2 and 2.5.

27. The kit according to claim 26, wherein the container containing the citric acid is a sachet.

28. The kit according to claim 25, wherein the container of the citric acid contains, in addition to the citric acid, other acceptable pharmaceutical or food additives, selected from the group formed by sweeteners, flavours, preservatives and colorants.

29. The kit according to claim 24, wherein the container containing the carbon-13 labelled urea is a flask which contains the suitable amount of carbon-13 labelled urea and the flask is of the appropriate volume to obtain the aqueous solution of carbon-13 labelled urea at the desired concentration.

30. The kit according to claim 24, wherein the container containing the carbon-13 labelled urea is a blister which contains a tablet, optionally dispersible, which contains the appropriate amount of carbon-13 labelled urea.

31. The kit according to claim 24, wherein the containers destined to containing the patient's breath are exetainers, which are constituted by a tube (1) made of glass, the stoppers of which (2) are threaded and have a septum (3) in the centre, made of an elastomer suited for pharmaceutical purposes, which permits its penetration by means of a needle which collects the air contained in the exetainer for its subsequent analysis.

32. The kit according to claim 24, wherein said means to blow the breath into the containers are straws.

33. The kit for the detection of *H. pylori*, suited for carrying out a method based on the carbon-13 labelled urea breath test, according to claim 1, which comprises a case which contains:
   a sachet containing citric acid, in the solid state, in a quantity sufficient so that, after dissolution in a suitable amount of water, it yields a pH comprised between 2 and 2.5, together with optionally, some additives, such as sweeteners, flavours, preservatives and colorants;
   a flask containing carbon-13 labelled urea selected among:
      i) a flask which contains the appropriate amount of carbon-13 labelled urea, said flask containing the necessary volume to dissolve the urea and achieve the desired concentration, or alternatively,
      ii) a blister containing a tablet, optionally dispersible, with the suitable amount of carbon-13 labelled urea;
   four exetainers destined to contain the breath of the patient, two of which are used to collect the patient's breath after the administration of the citric acid but before the administration of the aqueous solution of carbon-13 labelled urea, while the other two will collect the patient's breath after the administration of the aqueous solution of carbon-13 labelled urea; and
   some straws to blow the breath into the exetainers.

34. The kit according to claim 33, wherein said sachet contains between 2 and 5 g of citric acid, optionally together with other additives, for its dissolution in the suitable amount of water.

35. The kit according to claim 33, wherein the flask which contains the carbon-13 labelled urea is a flask of, at least, 20 to 50 ml, which contains between 50 and 100 mg of carbon-13 labelled urea.

36. The kit according to claim 33, wherein said tablet contains between 50 and 100 mg of carbon-13 labelled urea.

37. The kit according to claim 33, wherein said exetainers are labelled so that it is possible to distinguish easily between the exetainers destined for use in collecting the breath from before the administration the carbon-13 labelled urea from those used to collect the breath from after the administration of the carbon-13 labelled urea.

* * * * *